United States Patent [19]
Hoang et al.

[11] Patent Number: 5,922,314
[45] Date of Patent: Jul. 13, 1999

[54] SKIN PREPARATION COMPOSITION

[75] Inventors: Minh Q. Hoang, Taylorsville; Mohammad A. Khan, Sandy, both of Utah

[73] Assignee: Becton, Dickinson and Company, Franklin Lakes, N.J.

[21] Appl. No.: 08/926,959

[22] Filed: Sep. 10, 1997

Related U.S. Application Data

[63] Continuation of application No. 08/522,811, Sep. 1, 1995, abandoned.

[51] Int. Cl.[6] .................................................. A61K 33/18
[52] U.S. Cl. ........................................ 424/78.35; 424/667
[58] Field of Search .............................. 424/78.08, 78.35, 424/667

[56] References Cited

U.S. PATENT DOCUMENTS

| | | | |
|---|---|---|---|
| 4,229,410 | 10/1980 | Kosti | 422/28 |
| 4,374,126 | 2/1983 | Cardarelli et al. | 514/772.6 |
| 5,456,745 | 10/1995 | Roreger et al. | 106/128 |

*Primary Examiner*—Peter F. Kulkosky
*Attorney, Agent, or Firm*—Arthur D. Dawson; Bruce S. Weintraub

[57] ABSTRACT

An antimicrobial film-forming composition which provides antimicrobial effectiveness to the skin, comprising ethyl alcohol, carboxylated polyacrylates, a cross linking agent, an adhesion promoting agent which can include a secondary solvent and an emollient, an active antimicrobial agent which can be either iodine or povidone iodine, a pluronic polyol and optionally, water. This composition prevents degradation of iodine in the composition and is easily removable from the skin.

14 Claims, No Drawings

SKIN PREPARATION COMPOSITION

This application is a continuation under 37 CFR §1.62 of application Ser. No. 08/522,811, filed Sep. 1, 1995, now abandoned.

This invention relates to improved skin preparation compositions and more particularly, film-forming compositions which are resistant to body fluids and provide long term antimicrobial effectiveness to the skin. The compositions of the present invention are particularly useful in the healthcare profession.

BACKGROUND OF THE INVENTION

A critical time when existing antiseptic preparation or materials lose effectiveness in providing necessary prophylaxis is during surgical procedures. In this instance, subdermal flesh and/or internal body organs may be exposed to microorganisms. A typical procedure is to apply a conventional antiseptic solution, lotion, etc., to the dermis prior to performing a surgical incision. Such prophylactic materials are subjected to body fluids such as blood, perspiration, urine, gastric fluids of high acidity, and the like, as well as alcohol or other sterilants common to surgical procedure. Conventional antiseptic preparations lack resistance to such fluids and thus are prone to removal during surgery. Similarly, after surgical closure, the possibility of infection exists, and protection of the wound is necessary. In this instance, resistance to perspiration, urine, water, and other fluids, and resistance to removal via contact with bandages and the like is highly desirable but often unobtainable with existing preparations.

Long term protection is desirable to prevent infection and also to reduce the frequency of antiseptic application. Similarly, antiseptic application is desirable for non-surgical procedures such as treatment of cuts, punctures, scratches, and the like where medical attention may or may not be sought, hypodermic inoculations treatment of non-human animal wounds or infection, and even as a protective coating for the hands of the medical practitioner to forestall the transmission of pathogens to his patients.

U.S. Pat. No. 4,374,126 discloses an iodine film-forming composition comprising ethyl alcohol and carboxylated polyacrylates, a disfunctional amide that cross-links the acrylate polymer, an adhesion promoter and an antimicrobial agent. This film-forming solution contains, preferably, 1.0 percent iodine, being an effective biocide.

The film-forming solution disclosed in U.S. Pat. No. 4,374,126, when applied to the skin, forms a thin, continuous film containing iodine. The film adheres to the skin and is not soluble in water or alcohol but remains permeable to water moisture and carbon dioxide. The film can, however, be removed by natural soap and water. The elemental iodine slowly leaches out of the film and keeps the skin in contact virtually sterile. The initial disinfection is provided by the alcohol which is a carrier of the composition.

However, there are several disadvantages to utilizing this solution. Although the film forming solution of U.S. Pat. No. 4,374,126 serves the above purpose very well, it has been found that the concentration of active iodine falls rather quickly with time, and when it reaches a level of approximately 50% to 60% of its original concentration. the degradation stops and the concentration of iodine levels off. Furthermore, the film is too sticky to the skin and is not easily removed by water or alcohol. This causes inconvenience to the healthcare personnel in removing the film from the patient Additionally, iodine leaches out of the film slowly from the film.

Therefore, it is desirable to produce a skin preparation composition which prevents iodine degradation and increases the effectiveness and shelf-life of the composition, as well as the ability to easily remove the film from the patient.

SUMMARY OF THE INVENTION

The present invention is an improved film-forming composition for use on the skin during surgical procedures by healthcare professionals, which provides antimicrobial effectiveness and is easily removable from the skin. The film-forming composition of the present invention desirably comprises ethyl alcohol, carboxylated polyacrylates, a crosslinking agent, an adhesion promoting agent, an active antimicrobial agent which is either iodine or povidone iodine, and a pluronic polyol. This composition can further comprise water. The adhesion promoting agent can contain a secondary solvent, an emollient, or mixtures thereof.

A significant advantage of the film-forming composition of the present invention is its use in the healthcare profession in surgical procedures, providing substantial antimicrobial effectiveness, as well as the ability to easily remove the film from the skin.

A further advantage of the film-forming composition of the present invention is that it prevents iodine degradation and increases the stability and effectiveness of the composition.

Another advantage of the present composition is that it provides an effective long lasting topical film containing antimicrobial agents which help to destroy infection of human and other animal tissue upon contact. Furthermore, the present composition can provide a number of days of continuous protection against bacterial and fungal infection with minimal irritation to the tissue where so applied and where said film is highly resistant to removal by body fluids, antiseptics, and alcohols, and is resistant to physical removal, but easily removed by soap and water. In addition the present composition, when applied, does not interfere in bodily processes incident to health. such as transpiration, and healing.

DETAILED DESCRIPTION OF THE INVENTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The film-forming composition of the present invention comprises in one embodiment.

(a) ethyl alcohol;

(b) carboxylated polyacrylates;

(c) a difunctional amide that cross links the acrylate polymer;

(d) an adhesion promoter;

(e) an antimicrobial agent; and (f) a poly (oxypropylene) poly (oxyethylene) condensate.

Preferably, ethyl alcohol is present in the film-forming composition in an amount from about 65% to about 90% by weight of the total composition.

The preferred antimicrobial agent for use in the film-forming composition is elemental iodine. Preferably, iodine is present in the film-forming composition in an amount from about 0.5% to about 3% by weight of the total composition.

In a further preferred embodiment, povidone iodine can be used instead of elemental iodine as the antimicrobial agent in the film-forming composition. Preferably, the povidone iodine utilized can be povidone iodine USP and is preferably present in the film-forming composition in an amount from about 5% to about 15% by weight of the total composition.

Thus in this preferred embodiment, povidone-iodine powder in accordance with the standards of The United States Pharmacopeia The National Fomulary, referred to herein as USP, published by United States Pharmacopeial Convention, Inc., Rockville, Md. is used. As defined in the USP, the powder contains between 9% and 12% available iodine if calculated on its dried basis. The K-value of the povidone used in the povidone-iodine is typically K-30. The percent weight of an available iodine in the aqueous solution of about 0.85% to 1.2%. The antimicrobial properties are provided entirely by the ability of the iodine portion of the povidone-iodine to kill microbes.

Povidone iodine USP, as utilized in the composition of the present invention is especially advantageous, because it prevents iodine degradation and increases the leaching rate of iodine from the film. Thus, the stability of the solution with respect to iodine degradation increases significantly. This in turn increases the effectiveness as well as the shelf-life of the composition. Thus the degradation of iodine is minimized. Since povidone iodine is soluble in water, the film can be easily removed by water if there is a need for taking the film off the skin, A suitable film forming carboxylated polyacrylic polymer is available commercially under the registered trademark Carboset 525 from the B.F. Goodrich Co.

It is observed that films utilizing a carboxylated polyacrylate are undesirably hard and brittle in situ and do not adhere well to living tissue, In order to ameliorate said hardness and brittleness it has been discovered that a lower molecular weight material of the same general polymeric structure is used, the preferred plasticizing materials being either Carboset 514, a water soluble substance which similarly crosslinks with a difunctional amide, or even lower molecular weight Carboset 515, which also crosslinks with a difunctional amide. In each case, said covalent crosslinks provide the essential physical and chemical properties. Said resulting films are flexible and soft, but possess adequate resistance to the above-listed environmental factors. Preferably, Carboset 525 is present in the film-forming composition in an amount of from about 6% to about 10% by weight of the total composition. Preferably, Carboset 514 (or Carboset 515) is present in the film-forming composition in an amount from about 0.01% to about 3.0% by weight of the total composition.

The primary crosslinking agents are ureas or difunctional amides, and preferably, urea. Preferably, urea (about 1% to about 3% aqueous) is present in the film-forming composition in an amount of from about 1% to about 3% by weight of the total composition.

In order to promote adhesion to the dermis, a secondary solvent has been found to be useful. A preferred embodiment is ethyl acetate which dissolves skin deposits, especially those of a lipid nature which retard good adhesion and stand, in a sense, as a barrier to actual film contact with the living dermis. Solvation of said lipids and other skin chemicals allows a degree of polymer penetration of the pore structure providing excellent mechanical bonding of said film with said dermis, Preferably, ethyl acetate is present in the film-forming composition in an amount of from about 1% to about 2% by weight of the total composition.

It has also been found useful to add an emollient to the composition. A preferred embodiment uses isopropyl myristate as an emollient to enhance "feel" (i.e., cosmetic elegance) and also to promote adhesion of the described composition. Preferably, isopropyl myristate is present in the film-forming composition in an amount of from about 1% to about 2% by weight of the total composition.

Within the composition of the present invention there may also be incorporated pharmaceutical agents such as analgesics, anti-arthritics, antineoplastics, anti-inflammatories, antiparasitics and antivirals.

In a preferred embodiment the poly (oxypropylene) poly (oxythylene) condensates is Pluronic L64 and is available from BASF, Wyandotte, Mich. Preferably, the pluronic polyol is present in the film-forming composition in an amount of from about 0.1% to 1.0% by weight of the total composition.

The compositions are formulated by solvating Carboset 525 and Carboset 514, or Carboset 515, in denatured alcohol and water. Once solution is achieved, ethyl acetate, propyl myristate, an antimicrobial agent as described above, and as necessary, a poly (oxypropylene) poly (oxythylene) condensate is added.

In another preferred embodiment, water can be a further component of the film-forming composition. Preferably, water can be present in the film-forming composition in an amount of from about 5% to about 15% of the total composition.

A composition of the present invention can be in several forms, including but not limited to, for example, a spray, an ointment, a wetted dressing, a lotion and a cream.

Several preferred embodiments are described below:

| A) Ingredients | Formulation by Weight % |
|---|---|
| Carboset 525 | 8.0 |
| Carboset 514 (or Carboset 515) | 2.0 |
| Urea (2% Aqueous) | 2.0 |
| Isopropyl Myristate | 1.0 |
| Ethyl Acetate | 1.0 |
| Ethanol | 84.44 |
| Iodine | 1.20 |
| Pluronic L64 | 0.36 |
| B) Ingredients | Formulation by Weight % |
| Carboset 525 | 8.0 |
| Carboset 514 (or Carboset 515) | 2.0 |
| Urea (2% Aqueous) | 2.0 |
| Isopropyl Myristate | 1.0 |
| Ethyl Acetate | 1.0 |
| Ethanol | 70.0 |
| Povidone Iodine USP | 10.0 |
| Water | 6.0 |
| C) Ingredients | Formulation by Weight % |
| Ethanol | 70.0 |
| Povidone Iodine USP | 10.0 |
| Water | 6.0 |
| Propylene Glycol | 2.0 |
| Povidone K-30 | 10.0 |
| Glycerin | 2.0 |
| D) Ingredients | Formulation by Weight % |
| Ethanol | 70.0 |
| Povidone Iodine USP | 10.0 |
| Water | 11.0 |
| Propylene Glycol | 2.0 |
| Glycerin | 2.0 |
| Povidone K-90 | 5.0 |

The following examples are not limited to any specific embodiment of the invention, but are only exemplary.

EXAMPLE 1

STABILITY TESTING OF THE FORMULATION

Formulations (Compositions A–E) described in Table 1 below were tested under accelerated aging conditions for the stability of iodine in the composition. Compositions A–D are formulations disclosed in the present invention. Composition E is a control and is a formulation of the kind disclosed in U.S. Pat. No. 4,374,126.

TABLE 1

Film Forming Solution Formulation By Weight Percent

| INGREDIENTS | A | B | C | D | E |
| --- | --- | --- | --- | --- | --- |
| Carboset 525 | 8.0 | 8.0 | — | — | 8.0 |
| Carboset 514 | 2.0 | 2.0 | — | — | 2.0 |
| Ethyl Acetate | 1.0 | 1.0 | — | — | 1.0 |
| Isopropyl Myristate | 1.0 | 1.0 | — | — | 1.0 |
| Ethanol | 84.44 | 70.0 | 70.0 | 70.0 | 85.0 |
| $CaCl_2$ (5% Aq.) | — | — | — | — | — |
| Urea (2% Aq.) | 2.0 | 2.0 | — | — | 2.0 |
| Pluronic L64 | 0.36 | — | — | — | — |
| Povidone Iodine USP | — | 10.0 | 10.0 | 10.0 | — |
| Iodine | 1.20 | — | — | — | 1.0 |
| Water | — | 6.0 | 6.0 | 11.0 | — |
| Propylene Glycol | — | — | 2.0 | 2.0 | — |
| Povidone K-30 | — | — | 10.0 | — | — |
| Glycerin | — | — | 2.0 | 2.0 | — |
| Povidone K-90 | — | — | — | 5.0 | — |

Each composition was prepared as follows:

MIXING PROCEDURE

1. In a suitable mixing vessel, ethanol was added first and then the remaining ingredients, except for Povidone Iodine or Povidone K-90.
2. The ingredients were mixed by stirring until all the ingredients were solubilized
3. Finally, Povidone Iodine or Povidone K-90 was added as appropriate.
4. Stirring was continued until a homogenous solution was obtained for each composition (A–E).

Table 2 below the demonstrates the degradation of iodine with time at 60° C. with respect to Compositions B–E. Table 3 below demonstrates degradation of iodine with time at 52° C., with respect to Compositions A and E.

TABLE 2

Degradation Of Iodine At 60° C.
Concentration Of Iodine In Percent

| Time in Days | B | C | D | E |
| --- | --- | --- | --- | --- |
| 0 | 1.21 | 1.05 | 1.14 | 0.835 |
| 7 | — | — | — | 0.483 |
| 14 | 1.23 | 0.933 | 1.09 | — |
| 28 | 1.20 | 0.920 | 1.08 | — |
| 35 | 1.20 | 0.94 | 1.08 | 0.510 |

TABLE 3

Degradation Of Iodine At 52° C.
Concentration Of Iodine In Percent

| Time in Days | A | E |
| --- | --- | --- |
| 0 | 0.91 | 0.835 |
| 7 | — | 0.592 |
| 21 | 0.67 | 0.510 |
| 42 | 0.67 | — |
| 75 | — | 0.499 |

It is very clear from the data in Tables 2 and 3 that the stability of the compositions with respect to iodine concentration increases in Compositions A, B, C and D when compared to the controls (Composition E). The degradation of iodine is apparently most prevented in Composition B.

The stability of Composition B was further tested over a period of three months with respect to the control, Composition E. The results of this test are shown below in

TABLE 4

Degradation Of Iodine At 45° C.
Concentration Of Iodine In Percent

| Time in Months | Composition B | Composition E |
| --- | --- | --- |
| 0 | 1.12 | 0.83 |
| 1 | 1.10 | 0.61 |
| 2 | 1.13 | 0.60 |
| 3 | 1.14 | 0.59 |

Thus, Composition B is clearly superior to Composition E.

EXAMPLE 2

EFFECTIVENESS TESTING

The antimicrobial effectiveness of Compositions A, B and E were tested by the "zone of inhibition" technique. The procedure for this test is described below.

1. Nutrient agar cups were prepared in large petri dishes, 6 cups per dish.
2. Each petri dish was seeded with a given target microorganism, and in this Example, S. Aureus, P. Aeruginosa, E. Coli, and C. Albicans. These are the standard microorganisms representing gram positives, gram negatives and fungus classifications.
3. Approximately 0.3 mls. of each solution was added to individual agar cups.
4. Each petri dish was incubated at 350° C. for 48 hours.
5. The dishes were removed and the zone of inhibition was measured from the edge of the cup to the nearest area of microbial growth. All results were measured in millimeters.

The results of the zones of inhibition tests are shown below in Table 5.

TABLE 5

Zone Of Inhibition In mm.

| | A | B | E |
| --- | --- | --- | --- |
| S. Aureus | 11 | 6 | 6 |
| P. Aeruginosa | 9 | 3 | 4 |
| E. Coli | 9 | 3 | 6 |
| C. Albicans | 18 | 5 | 7 |

As can be seen, the compositions tested are all effective against common microorganisms with Composition A being the most effective.

EXAMPLE 3

WATER WASHABILITY

Based on water washability tests of Compositions B and E, performed on human subjects, it was found that Composition E was not washable with water or alcohol. Film from Composition B was found to be removable with water.

The water washability tests were conducted with 6 human subjects. Composition B was applied by a cotton swab application on the arm or the backs of the hands of each subject. Composition B was allowed to dry until a smooth shiny brown rubbery film remained on the skin. The film was washed off with potable cold tap water using fingers of the opposite hand to manually scrub the skin surface with the film. After rubbing the area painted with the film, the film disintegrated and was removed. After washing the area further with tap water, no sign of film was found on the area of skin where the film had been.

Thus, all the individuals painted with Composition B were able to wash off Composition B using only water and a light scrubbing action with their fingers. All individuals treated with Composition E were unable to wash the remaining film off with either water or alcohol.

EXAMPLE 4

BIOCOMPATIBILITY

Compositions marked B and E (the control) were tested for primary skin irritation and guinea pig skin sensitization. The results are summarized below.

TABLE 6

BIOCAMPATIBLITY OF COMPOSITIONS

| TESTS PERFORMED | COMPOSITION B | COMPOSITION E |
|---|---|---|
| Primary skin irritation | Negligible Irritant | Mild Irritant |
| Guinea Pig Dermal Sensitization | Non-sensitizer | Non-sensitizer |

Again, Composition B is clearly superior when compared to the control. The above results are based on the following information.

1. PRIMARY DERMAL IRRITATION TEST a. Composition B

OBJECTIVE: To evaluate the skin irritation potential of a test article.

TEST ARTICLE PREPARATION:

The sample, Composition B from Iodophor Swab Stick, was applied directly to the animal.

TEST SYSTEM:

Healthy, female New Zealand white rabbits were obtained from an appropriate vendor. Animals were individually housed and identified by an ear tag.

EXPERIMENTAL METHODS:

Prior to application of the sample, the rabbits' backs were clipped free of fur. Two sites were chosen on each rabbit, with the skin left intact on one site and the skin abraded on the other site. The test article was applied to the test site according to package instructions. The applicator swabstick was used to apply the solution in a circular motion to an approximate 1 inch×1 inch area. The area was covered with a gauze patch, and wrapped with an occlusive binder. After 24 hours, the binder was removed and an evaluation of the skin for erythema and edema was performed. A subsequent evaluation was performed 72 hours post-application.

TABLE 7

| | | DERMAL REACTION | | | |
|---|---|---|---|---|---|
| | | 24 Hours | | 72 Hours | |
| Test Animal | Reaction | Abraded | Intact | Abraded | Intact |
| 1 | Erythema | 0 | 1 | 0 | 0 |
| | Edema | 0 | 0 | 0 | 0 |
| 2 | Erythema | 0 | 1 | 0 | 0 |
| | Edema | 0 | 0 | 0 | 0 |
| 3 | Erythema | 1 | 0 | 0 | 0 |
| | Edema | 0 | 0 | 0 | 0 |
| 4 | Erythema | 1 | 2 | 0 | 0 |
| | Edema | 1 | 1 | 0 | 0 |
| 5 | Erythema | 0 | 1 | 1 | 1 |
| | Edema | 0 | 0 | 0 | 0 |
| 6 | Erythema | 0 | 0 | 0 | 0 |
| | Edema | 0 | 0 | 0 | 0 |

EVALUATION OF SKIN REACTIONS

| ERYTHEMA AND ESCHAR FORMATION: | Value | EDEMA FORMATION: | Value |
|---|---|---|---|
| No erythema | 0 | No edema | 0 |
| Very slight erythema (barely perceptible) | 1 | Very slight edema (barley perceptible) | 1 |
| Well-defined erythema | 2 | Slight edema (edges of area well defined by definite raising) | 2 |
| Moderate to severe erythema | 3 | | |
| Severe erythema (beet redness to slight eschar formation injuries in depth) | 4 | Moderate edema (raised approximately 1 millimeter) | 3 |
| | | Severe edema (raised more than 1 millimeter and extending beyond the area of exposure) | 4 |

TABLE 7-continued

DATA ANALYSIS:

| INDEX | EVALUATION |
|---|---|
| 0.0 | Nonirritant |
| >0.0–0.5 | Negligible Irritant |
| >0.5–2.0 | Mild Irritant |
| >2.0–5.0 | Moderate Irritant |
| >5.0–8.0 | Severe Irritant |

Subtotal Irritation Value for Erythema or Eschar Formation = 9
Subtotal Irritation Value for Edema = 2

Subtotal Irritation Value (Erythema) + Subtotal Irritation Value (Edema) = Total Irritation Score
9 + 2 = 11

$$\text{Primary Dermal Irritation Index}(PDII) = \frac{\text{Total Irritation Score}}{24} = \frac{0}{24} = 0.46$$

SUMMARY/CONCLUSION:

Based on a Primary Dermal Irritation Index of 0.46, the test article, Composition B, is considered a negligible irritant in rabbits.

b. Composition E

The skin irritation potential of Composition E was then tested.

TEST ARTICLE PREPARATION:

The test article, Composition E, was applied undiluted.

TEST SYSTEM:

Healthy, female New Zealand white rabbits were obtained from an appropriate vendor. Animals were individually housed and identified by an ear tag.

EXPERIMENTAL METHODS:

Prior to application of the sample, the rabbit's backs were clipped free of fur. Two sites were chosen on each rabbit, with the skin left intact on one site and the skin abraded on the other site, To reflect the end use of the test article, the Iodine Film Forming solution was applied undiluted, using the swab provided in the package. A generous amount of the solution was applied to each test site in an approximately 1"×1" area. The solution was allowed to dry Each test site was then wrapped with an occlusive binder. After 24 hours, the binder was removed and an evaluation of the skin for erythema and edema was performed. A subsequent evaluation was performed 72 hours post-application.

RESULTS: See Table 8, below.

TABLE 8

DERMAL REACTION

| | | 24 Hours | | 72 Hours | |
|---|---|---|---|---|---|
| Test Animal | Reaction | Abraded | Intact | Abraded | Intact |
| 1 | Erythema | 1 | 1 | 1 | 1 |
|   | Edema | 0 | 0 | 0 | 0 |
| 2 | Erythema | 0 | 0 | 2 | 2 |
|   | Edema | 0 | 0 | 0 | 0 |
| 3 | Erythema | 1 | 0 | 1 | 0 |
|   | Edema | 0 | 0 | 0 | 0 |
| 4 | Erythema | 1 | 1 | 0 | 0 |
|   | Edema | 0 | 0 | 0 | 0 |
| 5 | Erythema | 1 | 0 | 0 | 0 |
|   | Edema | 0 | 0 | 0 | 0 |
| 6 | Erythema | 1 | 0 | 1 | 0 |
|   | Edema | 0 | 0 | 0 | 0 |

EVALUATION OF SKIN REACTIONS

| ERYTHEMA AND ESCHAR FORMATION: | Value | EDEMA FORMATION: | Value |
|---|---|---|---|
| No erythema | 0 | No edema | 0 |
| Very slight erythema (barely perceptible) | 1 | Very slight edema (barley perceptible) | 1 |
| Well-defined erythema | 2 | Slight edema (edges of area well defined by definite raising) | 2 |
| Moderate to severe erythema | 3 | | |
| Severe erythema (beet redness to slight eschar formation injuries in depth) | 4 | Moderate edema (raised approximately 1 millimeter) | 3 |
| | | Severe edema (raised more than 1 millimeter and extending beyond the area of exposure) | 4 |

TABLE 8-continued

DATA ANALYSIS:

| INDEX | EVALUATION |
|---|---|
| 0.0 | Nonirritant |
| >0.0–0.5 | Negligible Irritant |
| >0.5–2.0 | Mild Irritant |
| >2.0–5.0 | Moderate Irritant |
| >5.0–8.0 | Severe Irritant |

Subtotal Irritation Value for Erythema or Eschar Formation = 15
Subtotal Irritation Value for Edema = 0
Subtotal Irritation Value (Erythema)   + Subtotal Irritation Value (Edema)   = Total Irritation Score
15                                      + 0                                     = 15

$$\text{Primary Dermal Irritation Index (PDII)} = \frac{\text{Total Irritation Score}}{24} = \frac{15}{24} = 0.6$$

SUMMARY/CONCLUSION:

Based on Primary Dermal Irritation Index of 0.6, the test article Composition E, is considered a mild irritant in rabbits.

2. CLOSED PATCH SKIN SENSITIZATION a. Composition E

OBJECTIVE: To assess the contact dermal sensitization potential of a test article.

TEST ARTICLE PREPARATION/EXTRACTION:

The test article, Composition E, was applied undiluted.

CONTROL ARTICLE:

A Positive Control (0.1% Dinitrochlorobenzene) is tested at least twice each year.

TEST SYSTEM:

Naive Hartley albino guinea pigs were used for this study. Animals were obtained from an appropriate vendor and weighed a minimum of 300 g when released from a 7-day acclimation period. Animals were individually housed and identified by a unique number placed on the cage card.

EXPERIMENTAL METHODS,

Prior to each induction, the upper flank skin of the guinea pigs was shaved. On Day 0, approximately 0.4 ml of the test article was applied to the test site via saturated Hilltop Chamber. The animals' trunk was securely wrapped with an occlusive binder. This procedure was repeated for each of the ten (10) test animals. After a six-hour contact period, the binders were removed.

Inductions 2 and 3 were conducted on Days 7 and 14, using the following procedure. The sample was applied per package instructions. The film former was applied directly to the test site with the swab contained in the package, allowed to dry, and then occluded. After Induction 3, the animals were rested for two weeks. At the termination of this rest period, the opposite upper flank of the ten (10) induced animals and five (5) naive control animals was shaved. Following the same procedure, a challenge application (6-hour contact) was done on each test and control animal.

Following the challenge application, observations of the test and control sites were done at 24- and 48-hours post-application. The sites were examined for erythema and edema, using the Draize method of scoring to grade reactions. Severity and incidence of reactions in the test and control groups were calculated.

$$\text{Incidence} = \frac{\text{\# of animals with scores} \geq 1 \text{ at either observation}}{\text{Total \# of animals}}$$

$$\text{Severity} = \frac{\text{Arithmetic total of all scores}}{\text{Total \# of animals}}$$

RESULTS/DATA ANALYSIS: See Tables 9, 10, 11 and 12.

TABLE 9

| EVALUATION OF SKIN REACTIONS | |
|---|---|
| Erythema and Eschar Formation | Value |
| No erythema | 0 |
| Very faint erythema, non-confluent | 0.5 |
| Very slight erythema, barely perceptible | 1 |
| Well-defined, moderate erythema | 2 |
| Moderate to severe erythema, with or without edema | 3 |

A ANALYSIS FOR COMPOSITION E:

TABLE 10

| TEST GROUP | | |
|---|---|---|
| | ERYTHEMA SCORE | |
| TEST ANIMAL | 24 HOUR | 48 HOUR |
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |
| 9 | 0 | 0 |
| 10 | 0 | 0 |

TABLE 11

NAIVE CONTROL GROUP

| | ERYTHEMA SCORE | |
|---|---|---|
| CONTROL ANIMAL | 24 HOUR | 48 HOUR |
| 1 | 0 | 0 |
| 2 | 0 | 0 |
| 3 | 0 | 0 |
| 4 | 0 | 0 |
| 5 | 0 | 0 |

TABLE 12

COMPOSITION E INCIDENCE AND SEVERITY INDICES

| Test Group: | Incidence | = 0/10 = 0 |
|---|---|---|
| | Severity | = 0/10 = 0 |
| Control Group: | Incidence | = 0/5 = 0 |
| | Severity | = 0/5 = 0 |

SUMMARY/CONCLUSION:

Based on the severity and incidence of the reactions observed at the 24 and 48-hours observations, Composition E is considered to be a nonsensitizer in guinea pigs.

b. Composition B

The contact dermal sensitization potential of Composition B was then assessed.

TEST ARTICLE PREPARATION/EXTRACTION:

The test article, Composition B, was applied directly to the animal.

CONTROL ARTICLE(S):

A Positive Control (0. 1% Dinitrochlorobenzene) is tested at least twice each year.

TEST SYSTEM:

Naive Hartley albino guinea pigs were used for this study. Animals were obtained from an appropriate vendor and weighed a minimum of 350 g when released from a 7-day acclimation period. Animals were individually housed and identified by a unique number placed on the cage card.

EXPERIMENTAL METHODS:

Prior to each induction, the upper flank skin of each of the guinea pigs was shaved. On Day 0, the test article was applied in a circular motion directly to the test site, using the applicator swab stick contained in the test article package. The test site was covered and secured to each animal's back with a gauze patch. The patch was covered with a piece of occlusive binding and the animal's trunk was securely wrapped with elastic tape. This procedure was repeated for each of the ten (10) test animals. After a six-hour contact period, the binders were removed.

Inductions 2 and 3 were conducted on Days 7 and 14, using the same procedure. After induction 3, the animals were rested for two weeks. At the termination of this rest period, the opposite upper flank of the ten (10) induced animals and five (5) naive control animals was shaved. Following the same procedure (for induction), a challenge application (6-hour contact) was done on each test and control animal.

Following the challenge application, observations of the test and control sites were done at 24- and 48-hours post-application The sites were examined for erythema and edema, using the Draize method of scoring to grade reactions. Severity and incidence of reactions in the test and control groups were calculated.

$$\text{Incidence} = \frac{\text{\# of animals with scores} \geq 1 \text{ at either observation}}{\text{Total \# of animals}}$$

$$\text{Severity} = \frac{\text{Arithmetic total of all scores}}{\text{Total \# of animals}}$$

RESULTS/DATA ANALYSIS: See Tables 9, 13, 14 and 15.

TABLE 13

TEST GROUP

| | ERYTHEMA SCORE | |
|---|---|---|
| TEST ANIMAL | 24 HOUR | 48 HOUR |
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |
| 9 | 0 | 0 |
| 10 | 0 | 0 |

TABLE 14

NAIVE CONTROL GROUP

| | ERYTHEMA SCORE | |
|---|---|---|
| CONTROL ANIMAL | 24 HOUR | 48 HOUR |
| 1 | 0 | 0 |
| 2 | 0 | 0 |
| 3 | 0 | 0 |
| 4 | 0 | 0 |
| 5 | 0 | 0 |

TABLE 15

COMPOSITION B INCIDENCE AND SEVERITY INDICES

| Test Group: | Incidence | = 0/10 = 0 |
|---|---|---|
| | Severity | = 0/10 = 0 |
| Control Group: | Incidence | = 0/5 = 0 |
| | Severity | = 0/5 = 0 |

SUMMARY/CONCLUSION:

Based on the severity and incidence of the reactions observed at the 24 and 48-hour observations, Composition B is considered to be a nonsensitizer in guinea pigs.

We claim:

1. An antimicrobial film-forming compound having improved iodine activity retention in shelf storage comprising:

(a) ethanol in an amount of 84.44 weight percent of the total composition;

(b) carboxylated polyacrylic polymer in an amount of about 10 weight percent of the total composition;

(c) urea (2% aqueous) in an amount of 2 weight percent of the total composition;

(d) isopropyl myristate in an amount of 1 weight percent of the total composition;

(e) ethyl acetate in an amount of 1 weight percent of the total composition;

(f) iodine in an amount of 1 weight percent of the total composition; and wherein the improvement comprises:

(g) poly(oxypropylene)poly(oxyethylene) condensate having a molecular weight about 2900 in amount of about 0.36 weight percent of the total composition.

2. An water washable antimicrobial film-forming composition having improved iodine activity retention in shelf storage comprises:

(a) ethanol in an amount of 70 weight percent of the total composition;

(b) carboxylated acrylic polymer in an amount of 1 0 weight percent of the total composition;

(c) urea (2% aqueous) in an amount of 2 weight percent of the total composition;

(d) ispropyl myristate in an amount of 1 weight percent of the total composition;

(e) ethyl acetate in an amount of 1 weight percent of the total composition; and wherein the improvement comprises:

(f) povidone iodine USP in an amount of 10 weight percent of the total composition; and (g) water in an amount of 6 weight percent of the total composition.

3. An antimicrobial film-forming composition having improved iodine activity retention in shelf storage comprising:

(a) ethanol in an amount of from about 65% to about 90% by weight of the total composition;

(b) carboxylated acrylic polymer in an amount from about 65% to about 93% by weight of the total composition;

(c) urea (about 1% to about 3% aqueous) in an amount of from about 1% to about 3% by weight of the total composition;

(d) isopropyl myristate in an amount of from about 1% to about 2% of the total composition;

(e) ethyl acetate in an amount of from about 1% to about 2% by weight of the total composition;

(f) iodine in an amount from about 0.5% to about 3% by weight of the total composition;

(g) a poly(oxypropylene)poly(oxyethylene) condensate having an average molecular weight of 2900 in an amount of from about 0.1% to about 1% by weight of the total composition.

4. The antimicrobial film-forming composition of claim 3 in the form of a spray.

5. The antimicrobial film-forming composition of claim 3 in the form of an ointment.

6. The antimicrobial film-forming composition of claim 3 in the form of a wetted dressing.

7. The antimicrobial film-forming composition of claim 3 in the form of a lotion.

8. The antimicrobial film-forming composition of claim 3 in the form of a cream.

9. An antimicrobial film-forming composition having improved iodine activity retention in shelf storage comprising:

(a) ethanol in an amount of from about 65% to about 90% by weight of the total composition;

(b) carboxylated acrylic polymer in an amount of from about 6% to about 13% of the total composition;

(c) urea (about 1% to about 3% aqueous) in an amount of from about 1% to about 3% by weight of the total composition;

(d) isopropyl myristate in an amount of from about 1% to about 2% of the total composition;

(e) ethyl acetate in an amount of from about 1% to about 2% by weight of the total composition;

(f) povidone iodine USP in an amount of from about 5% to about 15% by weight of the total composition;

(g) water in an amount of from about 5% to about 15% by weight of the total composition.

10. The antimicrobial film-forming composition of claim 9 in the form of a spray.

11. The antimicrobial film-forming composition of claim 9 in the form of an ointment.

12. The antimicrobial film-forming composition of claim 9 in the form of a wetted dressing.

13. The antimicrobial film-forming composition of claim 9 in the form of a lotion.

14. The antimicrobial film-forming composition of claim 9 in the form of a cream.

* * * * *